United States Patent [19]
Crowley

[11] Patent Number: 5,131,397
[45] Date of Patent: Jul. 21, 1992

[54] IMAGING SYSTEM FOR PRODUCING ULTRASONIC IMAGES AND INSONIFIER FOR SUCH SYSTEMS

[75] Inventor: Robert J. Crowley, Wayland, Mass.

[73] Assignee: Boston Scientific Corp., Watertown, Mass.

[21] Appl. No.: 579,010

[22] Filed: Sep. 7, 1990

[51] Int. Cl.$^5$ .............................................. A61B 8/12
[52] U.S. Cl. .................................................. 128/662.06
[58] Field of Search ................. 128/660.04–660.05, 128/662.03, 662.04, 662.05, 662.06

[56] References Cited

U.S. PATENT DOCUMENTS

| | | | |
|---|---|---|---|
| 3,810,459 | 5/1974 | Beches | 128/662.04 |
| 4,407,294 | 10/1983 | Vilkomerson | 128/662.05 |
| 4,431,005 | 2/1984 | McCormick | 128/656 |
| 4,431,006 | 2/1984 | Trimmer et al. | 128/662.05 |
| 4,501,277 | 2/1985 | Hongo | 128/660.05 |
| 4,546,771 | 10/1985 | Eggleton et al. | 128/662.05 |
| 4,706,681 | 11/1987 | Breyer et al. | 128/642 |
| 4,821,731 | 4/1989 | Martinelli et al. | 128/662.06 |

*Primary Examiner*—Francis Jaworski

[57] ABSTRACT

An imaging system and an insonifier for detecting the position and orientation of devices adapted to produce intravascular ultrasonic images from a human body, especially from an artery. The system includes a catheter having a pair of transducers rotate about the axis of the catheter. One of the transducers is for transmitting ultrasound and the other is for receiving the transmitted sound. The insonifier includes a third transducer that transmits sound at a frequency that can be received by the transducer in the catheter and is operatively associated with the catheter to provide sound at the same frequency as the first transducer. The sonogram that is produced can be displayed on a CRT and is the product of image detected by receiver in the catheter. Both images are simultaneously displayed to form a composite which enables the user to determine the position and the orientation of the tip of the catheter.

10 Claims, 3 Drawing Sheets

IMAGING SYSTEM FOR PRODUCING ULTRASONIC IMAGES AND INSONIFIER FOR SUCH SYSTEMS

FIELD OF THE INVENTION

The present invention relates to a system for determining the location and orientation of intravascular ultrasound images relative to the external anatomy of the organ being studied and an insonifier that is especially useful in the system.

1. Background of the Invention

Ultrasound imaging catheters provide for cross-sectional views of lumenal structures and are especially useful in the diagnosis of obstructive diseases that affect the vascular system in humans. Although there are various ways to accomplish this type of imaging, most ultrasound imaging catheters employ mechanisms to direct scanning beams of ultrasonic energy into the area being studied and receive the return echoes from these beams in a sequence for display on a cathode ray tube (CRT). Equipment that generates the sound and receives the return echoes so that the sound can be displayed on the CRT is well known.

One of the more troublesome problems encountered during medical examinations using ultrasound imaging catheters is the difficulty encountered in subsequently returning to the exact same site and with the same orientation of the tip if a second examination of the same area of the organ being studied is required. When the second examination of the organ is necessary the orientation of the ultrasound image displayed on the CRT might bear no relationship to the external anatomy of the catheterized body because insertion of the catheter subjects it to twists, bends and other conditions that make the orientation of the tip difficult or impossible to predict accurately. Thus, although the position of the catheter can be determined generally by X-ray, the physician cannot identify its orientation easily from the image on the CRT, that is whether the image being transmitted from the catheter to the CRT is "up", "down" or somewhere in between.

Knowledge of the "up/down" positioning is important especially when a sequence of ultrasound images is prepared for display in a series so as to provide images that, when grouped together, can generate an approximation of a three dimensional depiction of the organ being studied.

2. Description of the Prior Art

Devices for using acoustical pulses to generate echo sounds relating to the internal and external features of various parts of the body have been known and described in the prior art. Martinelli et al, U.S. Pat. No. 4,821,731, describes an electro-acoustical transducer device positioned on the tip of a catheter. The transducer device can be inserted into a liquid filled body canal or cavity. The catheter is moved into position at a particular site in the body and the transducer generates acoustical pulses in the directions of interest which can be displayed on a CRT.

Such devices include an acoustical output pulse generator and a receiver to detect the pulses in the form of echoes. From surface discontinuities in the form of impedance mismatches and the ultrasonic frequency of the precise part of the body at which the pulse is directed, an image of the portion of the body being examined can be displayed on the CRT. The pulses provide information about the tissue through which the pulses travel and the relative timing of the return pulses corresponds to impedance discontinuities which provide information on the thickness of various types of tissues at the specific location at which the initial pulse is directed. The relative strength of the echoes reflects the differences in impedance between adjacent boundaries of different types of tissues and therefore the difference in densities of the material. The acoustical technique can therefore be used to ascribe the character of tissues from which the echoes are received.

The information that is generated is particularly useful in procedures such as removing arteriosclerotic plaque deposits which restrict the flow of blood in coronary arteries. By moving the tip of the catheter to the location that is being studied, the plaque deposits can be identified. When the sites of the plaque or other irregularities are determined, the obstructions can be removed. Frequently, techniques such as laser radiation can be used in which an optical fiber or fibers are used to vaporize the plaque through known techniques. The plaque can thus be removed without the trauma associated with surgery. Such procedures, however, require specific knowledge of the location, thickness and density of the plaque to be removed in order to minimize damage to the arterial wall of the diseased site.

Fairly complicated mechanisms to identify the site precisely have been disclosed and include x-ray detection, the use of external magnetic fields or systems and methods for collecting sets of data derived from acoustical signals generated at a corresponding plurality of locations at the diseased site and relating the sets of data with respect to the relative locations from which they are obtained so that they can be used to create a coherent image of the diseased site.

Exemplary of such systems is the Martinelli et al apparatus that includes a catheter which is partially inserted into the body so that the tip is positioned relative to the preselected site and imaging data relating to the internal features can be acoustically determined by moving the tip to a plurality of positions relative to the site. An acoustical signal can be generated when the tip is in each of the positions. The acoustical energy responsive to the acoustical signal at each of the positions is sensed so as to create a set of data and the location is sensed magnetically in each of the positions. The sensed data and the respective positions from which each was obtained is related to create an image of the internal features of the organ being studied.

In the prior art system, the creation of an image of an arteriosclerosis lesion on the interior wall of an artery is accomplished by longitudinally and rotationally displacing the catheter tip (and thus the transducer in the catheter tip) through the diseased site so that a set of return pulses is obtained from a series of locations within the diseased site. The set of return pulses obtained from each angular and longitudinal position of the catheter can then be related to one another so as to create relative spatial information of the structure of the portions of the diseased site represented by sets of return pulses based on the known signatures of various types of tissue encountered in such diseased sites. The orientation of the tip of the catheter is accomplished by sensing the orientation of magnetic fields. The equipment necessary to provide for such views and their orientations is complicated and bulky, at best.

SUMMARY OF THE INVENTION

According to the present invention, I have discovered a novel imaging system including a catheter tip having transducers housed inside and an insonifier for detecting both the position and orientation of a catheter tip when it has been inserted into an organ or canal of the body. The system of my invention can display images of cross-sections of the organ or canal on a CRT and the CRT can also display the orientation of the tip simultaneously.

One part of the system includes a catheter which has a longitudinal axis, a tip and a proximal end. Sonic image generating means and an image sensing means in the form of transducers are disposed in the tip of the catheter. An insonifier forms another part of the system and is placed externally to the portion of the body being examined. The insonifier includes a sonic generator which produces sound at a frequency that can be received by the image sensing means housed in the catheter tip.

The insonifier has two modes of operation. In the first mode, a wide angle of ultrasound energy is generated at a frequency that can be received and displayed by the image sensing means which is housed in the catheter that is placed inside the body. In operation, the wide angle ultrasound from the insonifier is urged against the outside of the body in the general area of where the catheter tip is thought to be. The representation of the wide angle sound will appear on the CRT and provide an interference pattern adjacent where the catheter tip is located. At the same time the sonic generator in the catheter is sending its own signals to the CRT. When the general area of the catheter is located, the ultrasound of the insonifier is focused so as to determine precisely where the catheter tip is located. At the same time, the orientation of the catheter tip becomes evident on the CRT through the signal that is generated by the insonifier and detected by the image sensing means. The pattern from the insonifier shows on the CRT because the externally applied field can be picked up by the transducer within the catheter that is disposed within the patient. The pattern is brightest when the insonifier is in closest proximity to the tip of the catheter. The pattern also has a directional characteristic which is due to the manner in which the sonic energy propagates through the tissue. The pattern forms a viewable image on the CRT that correctly indicates the orientation of the catheter tip relative to the insonifier.

The most efficient transfer of sonic energy from the insonifier to the image sensing means occurs when the two devices face each other. By knowing the orientation of one of the devices, the position at any given time of either of them can be determined. The viewable image of the insonifier can be a bright light which shines to the area of the image and corresponds to the direction of the insonifier. If the display imaging system, the CRT, is equipped with a means to rotate image electronically, then the orientation (up, down, etc.) can be displayed correctly and repeatedly together with a knowledge of the exact position of the catheter tip. A marking device can be added to the insonifier to mark and identify permanently where the catheter is relative to the outside of the body.

DESCRIPTION OF THE PREFERRED EMBODIMENTS

Figure 1:
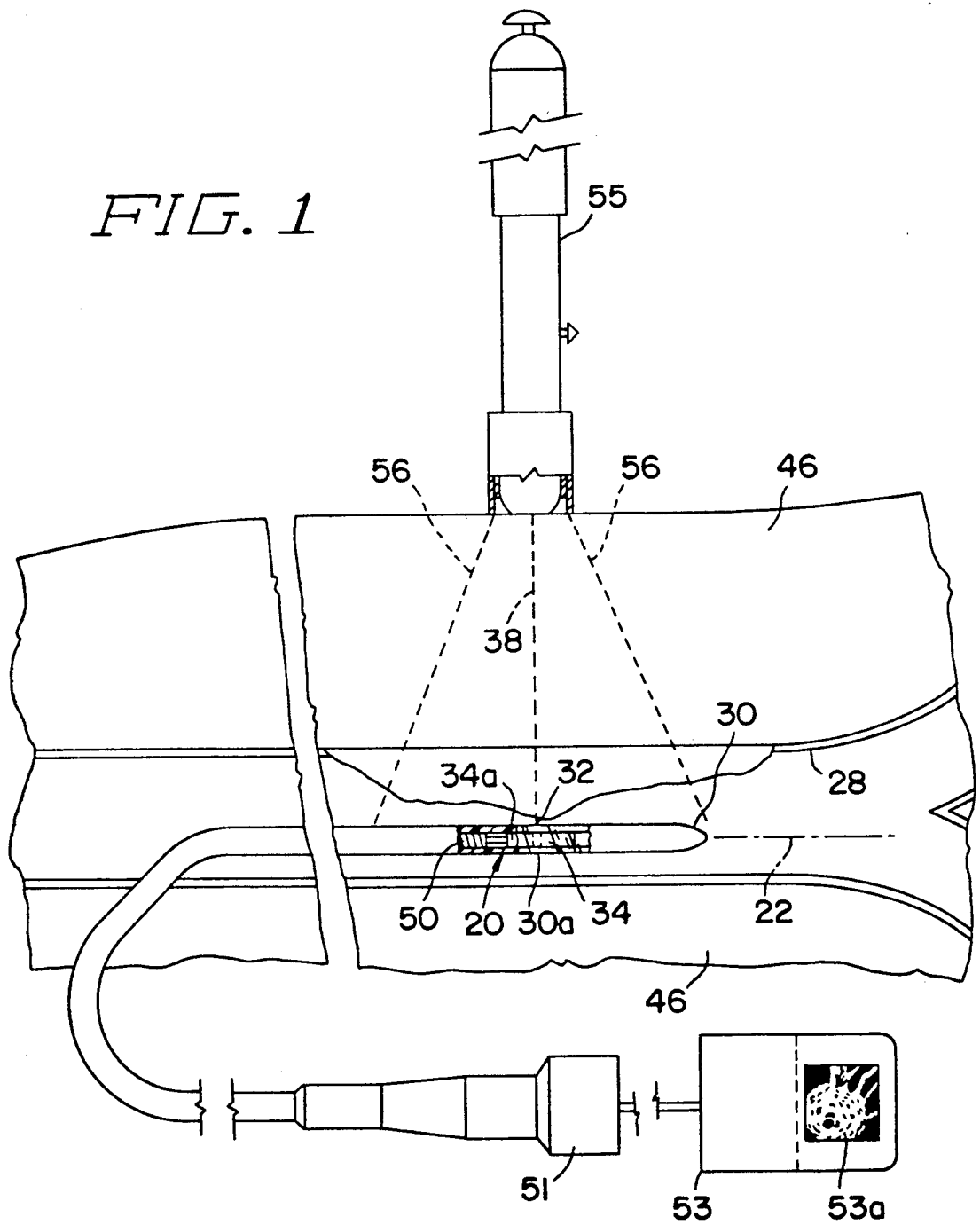
FIG. 1 is a view of the system, partially in cross section, according to the present invention including a catheter disposed in an artery, an insonifier and related electro-acoustical transmission and display devices.

Referring to FIG. 1, the catheter 20 is shown disposed within an artery 28 with the tip section 30 positioned opposite a stenotic lesion shown at 32. A transducer 34 disposed in the tip section 30 is positioned to transmit a beam of acoustical pulses from tip section 30 transversely to the longitudinal axis 22 of catheter 20 preferably through a window 30a. Sonic pulses are generated in response to electrical pulses transmitted along a set of insulated electrical conductors (not shown) that are disposed within a cable 50. The generation and receiving of sound can be produced by the transducer 34 which can be a single transducer that is switched back and forth between a transmission mode and a receiving mode. Preferably, however, a set of transducers 34 and 34a is used, one connected for transmission and the other for receiving. The acoustical pulses will be transmitted along a radius of transmission 38 and pass into a lesion 32 and the underlining arterial wall 28. Acoustical echos, deflected by impedance mismatches of the various surfaces of the different substrates return to the transducer 34 (or 34a) and are converted to electrical signals which are transmitted through the conductors in the cable 50. The transducer is preferably disposed within the tip section 30 and can rotate about the longitudinal axis 22. Such rotation is accomplished by turning cable 50 with a motor 51. Motor 51 and the use of a transducer disposed in a catheter on a rotatable cable is well known.

In the usual operation of ultrasonic image producing catheters and display of the image, a motor controller positions the transducer 34 for the next scan line. Within a conventional unit 53, a transmit pulser drives the ultrasound transducer. The transducer 34 converts the electrical energy to acoustical energy and emits a sound wave at a predetermined frequency. The sound wave reflects off the section 32 of the organ being studied. A portion of the sound wave returns to the transducer 34 (or to a second transducer 34a placed in close proximity to the first one). The acoustical energy is reconverted to electrical energy. A receiver in the unit 53 takes a waveform of the electrical energy and gates out the originally transmitted pulse. The remaining information is processed so that signal amplitude is converted to intensity, and time from the originally transmitted pulse and the signal is translated to distance. The brightness and distance information is transmitted into a vector/scan connector which, together with the position information from the motor controller, converts the polar coordinates to rectangular coordinates for a raster monitor. The process is repeated many thousands of times per second to form a real time, two dimensional ultrasound image of the subject being studied and for display on a CRT 53a and recording.

In addition to the image of the anatomy displayed on the CRT 53a from the transducers in the catheter, an interfering second image generated by the insonifier 55 is simultaneously displayed on the CRT 53a. As set out previously, the sonic emissions for the second image are produced by the insonifier 55 and are shown as dotted lines 56. In the illustrated example, an wide angle signal is produced by the insonifier 55 which enables the user to apply the device in the general area of the body 46 where the catheter tip 30 is thought to be. Once the insonifier 55 has been located in the general region of the catheter tip 30, an interference signal will show on the CRT. When the area is generally located, the emission from the device 55 can be focused so as to produce a narrower signal thereby to provide a bright area on the CRT which will more closely correspond to the relative position of the device 55 and the tip 30 of the catheter. Then, with an appropriate adjustment, the "top" of the organ being examined can be adjusted on the CRT as desired. As can be seen from the drawing, in the preferred embodiment there is no electrical connection between the unit 53 and the insonifier 55, although in some instances it may be desirable to use a wand that is pulsed from a common pulse generator in unit 53 for supplying a pulse to both the insonifier 55 and the transducer 34. The signal from the insonifier 55 should preferably be pulsed so as to conserve power since the insonifier 55 is battery powered and continuous operation of the insonifier 55 will quickly reduce its output. In those cases where it is found to be more efficacious to use pulses in each transducer generated from a single source, an electrical connection is required between the insonifier 55 and unit 53.

Figure 2:
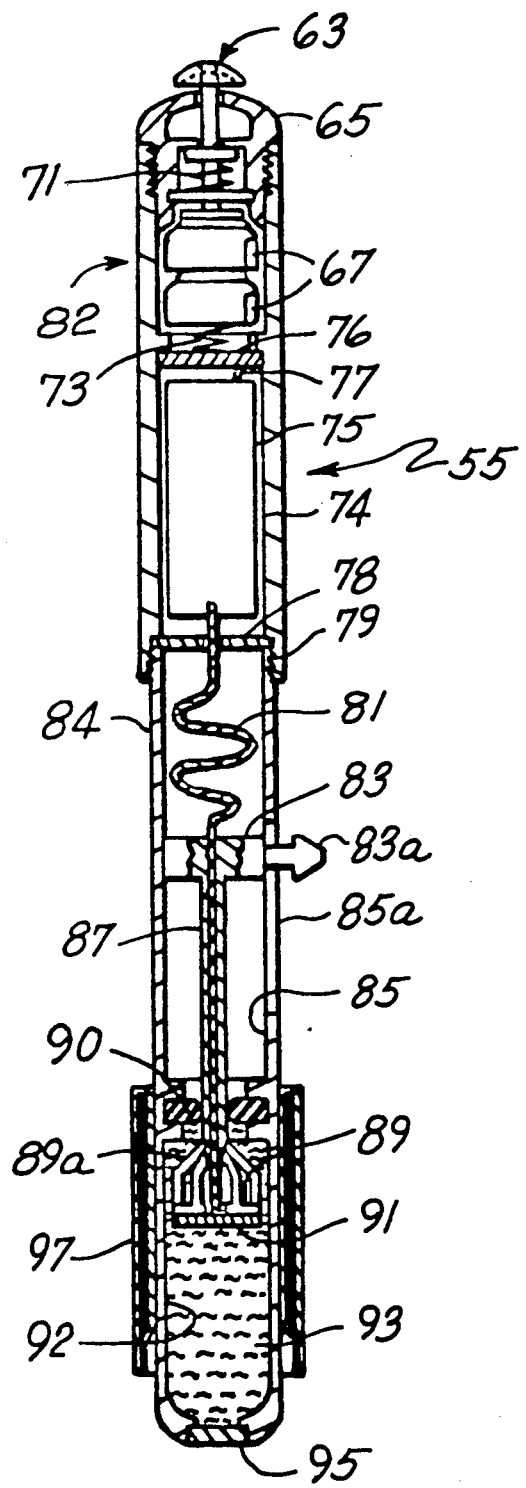
FIG. 2 is a cross-sectional view of an insonifier having a dual range acoustical transmission that can be used with the system of the present invention.

Referring to FIG. 2, an embodiment of the sonic insonifier of the present invention is shown. The preferred embodiment of the insonifier has a tubular barrel with an operating end 82 and an examining end 84. The operating end 82 is connected to the examining end 84 by means of threads 79 and a male to female fitting. An on/off button 63 slides within a collar 65 that is attached, preferably by threads, to the end of operating end 82. The collar 65 can be unscrewed to enable the user to reach a battery set 67 for their replacement. Button 63 is normally biased in the "off" position by a spring 71, as is conventional with many battery operated devices. The battery set 67 sits upon a spring 73 that rests on a wall 76.

A chamber 74 disposed within the operating end 82 houses a conventional pulse generator circuit disposed on a circuit board 75. Electrical connection between the battery set 67 and the pulse generator circuit board 75 is accomplished through wire 77.

A coaxial wire 81 extends from the circuit board 75 and the upper chamber 74 through a wall 78 to the top of a plunger 83. Coaxial cable 81 is of a sufficient length to provide for motion of the plunger 83 along the axis of a lower chamber 85. The plunger 83 has a knob 83a that extends outwardly from lower chamber 85 and is moveable in a slot 85a. A hollow stem 87 extends from plunger 83 and receives the coaxial cable 81. A support plate 89, preferably supported by knees 89a, is disposed on the end of the stem 87 and within the examining end 84 of the insonifier. A transducer 91 is disposed on the support plate 89 and is connected to coaxial cable 81. The tip of examining end 84 forms a fluid holding chamber 92 and is filled with fluid 93 commonly used for the transmission of sound. Fluids may be, for example, water, oil or silicones. To keep the fluids within the chamber 92, stem 87 rides within an 0-ring seal 90 which prevents leaking. A window 95, generally formed of plastic that is transparent to sonic waves, is disposed in the tip.

Movement of the plunger 83 relative to window 95 moves transducer 91 relative to the window 95. When the transducer 91 is most distantly positioned relative to window 95, the sonic radiation is most sharply in focus. As it is moved nearer to the window 95, the focus is reduced, but the area that is being irradiated is wider. Thus, the insonifier 55 can be moved around over a wide area with the transducer 91 nearest the window 95 until the interference signal shows on the CRT. Then the focus can be narrowed by moving the transducer 91 away from the window 95 to determine the precise location of the catheter tip.

In order to identify permanently the exact location of where the catheter is on the inside of the body, a marking sleeve 97 is used that is slidably disposed around the end of the examining end 84. The marking sleeve 97 can include a felt tip 97a with an ink supply. When the interference signal is seen by the operator of the equipment on the CRT 53a, and when the catheter has been precisely located, the sleeve 97 can be moved along the examining end 85 and can mark the precise location on the skin for subsequent use. Conventional marking inks can be used at the end of the sleeve 97 to accomplish the marking.

Figure 3:
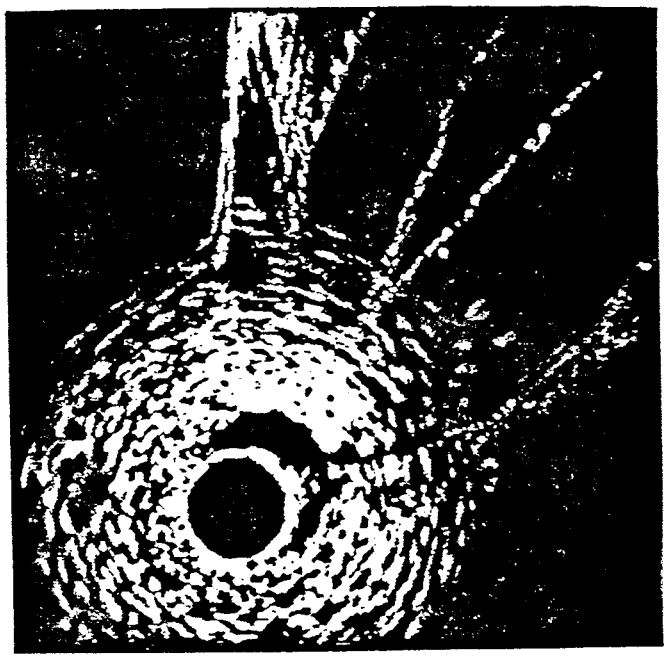
FIG. 3 is a view of a sonogram as displayed on a an ultrasound imaging console cathode ray tube whereby the orientation of the catheter can be determined by an interference signal generated by the insonifier.

Referring to FIG. 3, a view is shown of an interference pattern overlaying a typical sonogram of an artery. In the sonogram, the circular dark area at the center is the lumen of the catheter. The circular bright area surrounding the dark area is the wall of the catheter. To the right of the bright area (between 12 and 5 o'clock) is a dark section that is the portion of the artery carrying blood and not occupied by the catheter. The walls of the artery are delineated as the line between the blood-containing dark section and the bright area surrounding it. A circular dark area is shown at 12 o'clock. This area represents a vein that is adjacent to the artery. The generally radial bright lines at 12, 1 and 3 o'clock are the interference pattern generated by the insonifier. With this visual representation of the interference pattern, it is possible for the operator to establish with certainty the orientation of the catheter in the artery being examined. With additional reduction of the focus of the insonifier, the interference pattern can be narrowed, as desired, or it can be converted electronically to an indicator such as an arrow.

It is apparent the modification and changes can be made within the spirit and scope of present invention. It is my intention, however, only to be limited by the scope of the appended claims.

As my invention I claim:

1. An imaging system for detecting the position and axial orientation of device adapted to produce intravascular ultrasonic images from a human body and to enable an operator of the system to reposition the device at the same location and axial orientation, said system comprising:

a catheter having a longitudinal axis, a distal end and a proximal end, said catheter further having a sonic image generating means and a sonic image sensing means disposed in the distal end thereof, said catheter being adapted to be disposed in a vascular organ of the body and being susceptible of random axial orientation within said vascular organ;

an insonifier disposed external to said body, said insonifier being operatively associated with said sonic image sensing means and providing sound at a frequency that can be detected and displayed by said sonic image sensing means;

means for displaying an image detected by said sonic image sensing means and simultaneously displaying on the same display the signal produced by said insonifier.

2. The system according to claim 1 wherein the sonic image generating means and said sonic image sensing means are rotatable about said longitudinal axis of said catheter whereby to generate an sonogram representing a cross section of the vascular organ being catheterized.

3. The system according to claim 1 further including in said insonifier a means to produce both narrow and wide angle ultrasonic waves.

4. The system according to claim 1 wherein acoustical energy generated by said insonifier has two stages, the first stage providing a wide flood of acoustical energy and the second stage having an insonifying beam of narrow focus whereby to enable the user to initially identify the general area being studied and then to focus clearly upon the precise area.

5. An imaging system according to claim 1 further including a marking means to mark the location of the insonifier on the outside of the body being examined.

6. An imaging system for detecting the position and axial orientation of a device adapted to produce intravascular ultrasonic images from a human body and to enable an operator of the system to reposition the device in the same location and axial orientation, said system comprising:

a catheter having a longitudinal axis, a distal end and a proximal end, said catheter having an image generating means and an image sensing means disposed in the distal end of said catheter, said catheter being adapted to be disposed in a vascular organ of the body and being susceptible of random axial orientation within said vascular organ;

an insonifier arranged external to said body, said insonifier being operatively associated with said image sensing means and providing sound that can be sensed and displayed by said image sensing means, said insonifier including a housing having an ultrasonically transparent tip, a proximal end, a distal end and a window disposed at said distal end, a chamber disposed in said housing at the distal end thereof, a sonic image generating means disposed in said chamber and a pulse generating means disposed in the proximal end to generate pulses for said sonic image generation means, and means connecting said pulse generating means to said sonic image generating means;

means for displaying an image detected by said image generating means and simultaneously displaying the image produced by said insonifier, the image produced by said insonifier being displayed as an interference signal so as to display the orientation of the catheter whereby the operator of the system can determine the axial orientation of the image generating and image sensing means.

7. An imaging system according to claim 6 further including a marking means to mark the location of the insonifier on the outside of the body being examined.

8. An insonifier adapted to provide for a display of axial orientation of an image produced by an ultrasound image device disposed within a human body, said insonifier comprising:

a housing having a ultrasonically transparent tip, a proximal end and a distal end;

a chamber disposed in said housing at the distal end thereof;

sonic image generating means disposed in said chamber, said sonic image generating means being movable on a longitudinal axis relative to said transparent tip from an advanced position where it can generate wide angle ultrasound transmissions that can be received as unfocused transmissions by the ultrasonic image generating device disposed within said body to a retracted position adjacent said transparent tip where it can generate focused sonic transmissions and can be received as focused transmissions by said device;

means to move said sonic image generating means from said retracted position to said advanced position;

pulse generating means disposed in the proximal end of said housing;

means connecting said pulse generating means to said sonic image generating means.

9. An imaging system according to claim 8 further including a marking means to mark the location of the insonifier on the outside of the body being examined.

10. The imaging system according to claim 8 wherein said sonic image generating means is a transducer disposed on a plunger movable on a longitudinal axis.

* * * * *